US012611329B2

(12) United States Patent
Yuan et al.

(10) Patent No.: US 12,611,329 B2
(45) Date of Patent: Apr. 28, 2026

(54) FLUID COLLECTION BOX FOR PHACOEMULSIFICATION SURGERY

(71) Applicant: Innolcon Medical Technology (Suzhou) Co., Ltd., Suzhou (CN)

(72) Inventors: Xiaohe Yuan, Suzhou (CN); Wei Luo, Suzhou (CN); Zhongyu Yan, Suzhou (CN); Zhenzhong Liu, Suzhou (CN)

( * ) Notice: Subject to any disclaimer, the term of this patent is extended or adjusted under 35 U.S.C. 154(b) by 490 days.

(21) Appl. No.: 18/547,114

(22) PCT Filed: May 19, 2022

(86) PCT No.: PCT/CN2022/093803
§ 371 (c)(1),
(2) Date: Aug. 18, 2023

(87) PCT Pub. No.: WO2022/247720
PCT Pub. Date: Dec. 1, 2022

(65) Prior Publication Data
US 2024/0050275 A1 Feb. 15, 2024

(30) Foreign Application Priority Data

May 26, 2021 (CN) .......................... 202110579673.7

(51) Int. Cl.
*A61F 9/007* (2006.01)
*A61M 1/00* (2006.01)

(52) U.S. Cl.
CPC ...... *A61F 9/00745* (2013.01); *A61F 9/00781* (2013.01); *A61M 1/62* (2021.05)

(58) Field of Classification Search
CPC .... A61M 1/62; A61F 9/00745; A61F 9/00781
See application file for complete search history.

(56) References Cited

U.S. PATENT DOCUMENTS 9,931,447 B2 * 4/2018 Layser ................... A61M 1/77
2013/0245543 A1 9/2013 Gerg et al.
2014/0323953 A1 * 10/2014 Sorensen ............ A61F 9/00745
604/35

FOREIGN PATENT DOCUMENTS

CN 106999641 A 8/2017
CN 110368533 A 10/2019
(Continued)

OTHER PUBLICATIONS

International search report corresponding to international application PCT/CN2022/093803 mailed Aug. 11, 2022 (7 pages).

*Primary Examiner* — Dung T Ulsh
(74) *Attorney, Agent, or Firm* — Armstrong Teasdale LLP

(57) ABSTRACT

The present disclosure discloses a fluid collection box for phacoemulsification surgery, including a case composed of a front plate, a body, and a rear plate. The case communicates with a waste liquid bag. The body has a perfusion passage and a suction passage that are disposed independently. The perfusion passage is a sealed circulation cavity defined by a cover and the body. The circulation cavity communicates with a first connection port and a second connection port on the body for perfusion. There is a gap between the cover and the body. Connection and disconnection of the perfusion passage is controlled by pressing the cover. The suction passage is a pipeline that communicates a third connection port with the waste liquid bag, and performs perfusion by a peristaltic pump. The suction passage further communicates with a negative pressure regulating loop, to regulate pressure within the suction passage. According to the present disclosure, the perfusion passage and the suction passage are independently disposed, so that the two do not interfere with each other and work independently. Meanwhile, it is ensured that pressure within the (Continued)

perfusion passage is stable, thereby reducing changes of intraocular pressure, and improving safety during use.

12 Claims, 6 Drawing Sheets

(56)                References Cited

FOREIGN PATENT DOCUMENTS

| | | |
|---|---|---|
| CN | 113180912  A | 7/2021 |
| WO | WO 2020225643  A1 | 11/2020 |

* cited by examiner

FLUID COLLECTION BOX FOR PHACOEMULSIFICATION SURGERY

FIELD OF THE INVENTION

The present invention relates to the technical field of medical instruments, and in particular to a fluid collection box for phacoemulsification surgery.

BACKGROUND OF THE INVENTION

With age, lenticular opacity or cataracts become quite common. Cataracts can be treated by replacing a clouding crystalline lens with an artificial crystalline lens. Ophthalmic phacoemulsification surgery is a relatively advanced cataract treatment technology for the moment. A phacoemulsification system typically uses ultrasound energy to break the crystalline lens and extract the crystalline lens from a capsular bag.

In a cataract surgery and other treatment processes for eyes, it is crucial to precisely control a fluid volume in the eye and intraocular pressure. Although the ultrasound energy can break the cataract and allow the cataract to be sucked into a therapeutic probe with suction function, it is necessary to introduce a corresponding flushing liquid into the eye, so that the total volume of a fluid in the eye would not change excessively. If the total volume of the liquid in the eye decreases during the process (pressure is excessively small), the eye may collapse and causing significant tissue damages. Similarly, excessive intraocular pressure may strain and damage tissues of the eye.

During the surgery, when the cataract at a needle is suddenly sucked, surges often occur. The surge can cause a rapid change to the intraocular pressure, which can easily cause damages to the eye.

In the existing ophthalmic surgery system, a surgery box that can cooperate with the system is usually used to implement perfusion and suction functions. However, in an existing technology, usually the perfusion function is implemented by gravity. As a result, the value of perfusion pressure cannot be detected in real-time. Moreover, in the existing technology, when surges occur, the liquid is usually enabled to flow from a perfusion passage into a suction passage, which can cause instability of the perfusion pressure and exacerbate changes of the intraocular pressure.

Therefore, how to ensure balance between an intraocular fluid volume and the intraocular pressure in the ophthalmic surgery is currently an urgent problem to be resolved.

SUMMARY OF THE INVENTION

An objective of the present invention is to overcome shortcomings of an existing technology, and to provide a fluid collection box for phacoemulsification surgery, which is achieved through the following technical solutions:

A fluid collection box for phacoemulsification surgery, comprising a case composed of a front plate, a body, and a rear plate. The case communicates with a waste liquid bag. The body has a perfusion passage and a suction passage that are disposed independently. The perfusion passage is a sealed circulation cavity defined by a cover and the body. The circulation cavity communicates with a first connection port and a second connection port on the body for perfusion. There is a gap between the cover and the body. Connection and disconnection of the perfusion passage is controlled by pressing the cover. The suction passage is a pipeline that communicates a third connection port with the waste liquid bag, and performs perfusion by a peristaltic pump. The suction passage further communicates with a negative pressure regulating loop to regulate pressure within the suction passage.

Preferably, a back surface of the cover is provided with a protruding rib extending downward along an edge thereof. The body is provided with a recess matching the protruding rib. The protruding rib is in an interference fit with the recess and there is a gap therebetween. A cavity wall of the circulation cavity is defined by the back surface of the cover and a surface of the body. A perfusion outlet and a perfusion inlet of the circulation cavity are both located on the body. The perfusion outlet communicates with the first connection port. The perfusion inlet communicates with the second connection port.

Preferably, the cover has an outer convex portion and an elastic portion. The outer convex portion is opposite to the perfusion outlet. The elastic portion is opposite to the perfusion inlet. In a first state, there is a gap between the outer convex portion and the perfusion outlet, to maintain liquid flow within the circulation cavity. In a second state, the outer convex portion is pressed to be closely attached to the perfusion outlet, to block the liquid flow within the circulation cavity. The elastic portion can deform during perfusion. The elastic portion is provided with a sensor to detect perfusion pressure within the circulation cavity through the generated deformation.

Preferably, the suction passage includes a first communication port and a second communication port on the body. The third connection port communicates with the first communication port. The waste liquid bag communicates with the second communication port. A pump line of the peristaltic pump is communicated between the first communication port and the second communication port. The pump line is disposed on a limiting mechanism on the body. The limiting mechanism includes a limiting groove fixedly disposed on the body and two fixed blocks clamped at two ends of the limiting groove. Each of the fixed blocks is fixedly connected to the pump line. Baffle plates are disposed on two sides of an extension direction of the pump line.

Preferably, the suction passage includes an accommodation cavity disposed on a back surface of the body. The accommodation cavity is a sealed chamber composed of the body, the rear plate, and a sealing ring. A liquid inlet of the accommodation cavity communicates with the second communication port. The accommodation cavity communicates with the waste liquid bag by communicating members.

Preferably, a separator is vertically disposed in the accommodation cavity, and the accommodation cavity is divided into a first chamber and a second chamber by the separator. The liquid inlet communicates with the first chamber. A top portion of the separator has a notch. The liquid in the first chamber enters the second chamber through the notch.

Preferably, the communicating members are two identical connecting pipes that are vertically disposed on an inner side surface of the rear plate. The two connecting pipes are respectively disposed in the first chamber and the second chamber. An input port of the connecting pipe is located at atop portion thereof, and an output port is located at a bottom portion of a side surface, where the connecting pipe and the rear plate connect. The output port is disposed opposite to and communicates with a through hole on the waste liquid bag.

Preferably, the negative pressure regulating loop is disposed on the surface of the body, and is composed of a reflux inlet, a reflux outlet, and a sealed passage. The reflux inlet communicates with the second chamber. The reflux outlet communicates with the third connection port. A cavity wall of the sealed passage is defined by a sealing cover and the surface of the body. The reflux inlet will be opened when it is detected that the suction passage is blocked. The reflux inlet will be closed when the suction passage is not blocked.

Preferably, a negative pressure value in the suction passage is measured by a negative-pressure sensor disposed on the surface of the body. The negative-pressure sensor is a sealed cavity composed of a deformable metal sheet and the surface of the body. The sealed cavity respectively communicates with the third connection port and the first communication port.

Preferably, a back surface of the rear plate is provided with a handheld annular component.

Beneficial effects of the present invention are mainly as below:

1. The perfusion passage and the suction passage are independently disposed, so that the two do not interfere with each other. When blockage occurs, the liquid in the cavity is accommodated by the suction passage to regulate the intraocular pressure. Meanwhile, it is ensured that pressure within the perfusion passage is stable, thereby reducing changes of the intraocular pressure, and improving safety during use.

2. The elastic portion of the cover of the perfusion passage deforms and expands during the perfusion. On one hand, elasticity of the elastic portion can alleviate generated impact when a perfusion fluid enters. On the other hand, a value of perfusion pressure can be detected in a real-time manner by using the magnitude of deformation of the elastic portion in cooperation with a sensor on the system.

3. The outer convex portion of the perfusion passage is disposed opposite to the perfusion outlet at positions. On one hand, positioning can be quickly performed when press is required to block the perfusion fluid; on the other hand, the gap between the perfusion passage and the perfusion outlet is increased, thereby ensuring the sufficient capacity of the perfusion passage.

4. The suction passage uses the peristaltic pump to implement a suction function. Suction with the peristaltic pump has better stability and safety. At the same time, the limiting mechanism is disposed to fix a position of the pump line, thereby effectively avoiding axial movement and twisting of the pump line during operation.

5. The suction passage communicates with the negative pressure regulating loop to avoid blockage in the suction passage, which can cause excessive internal negative pressure. In this way, eye collapse and unnecessary tissue damages can be prevented, thereby ensuring safety of the surgery and reducing risks.

6. The negative-pressure sensor is further disposed on the suction passage. A property that the metal sheet is deformable is used to reflect the negative pressure in the suction passage in real-time, and the value of the negative pressure is monitored in real-time through the deformation of the metal sheet. Moreover, opening or closing of the negative pressure regulating loop is controlled by the detected negative pressure, thereby improving precise control of the pressure within the suction passage.

7. The separator is disposed vertically in the accommodation cavity. The disposing of the separator can block large particles in a suction pipeline in the first chamber, thereby can function as a filter, and can prevent the large particles from entering the suction pipeline through the reflux inlet.

BRIEF DESCRIPTION OF THE DRAWINGS

Technical solutions of the present invention are further described below with reference to the accompanying drawings.

DETAILED DESCRIPTION OF THE EMBODIMENTS

Figure 1:
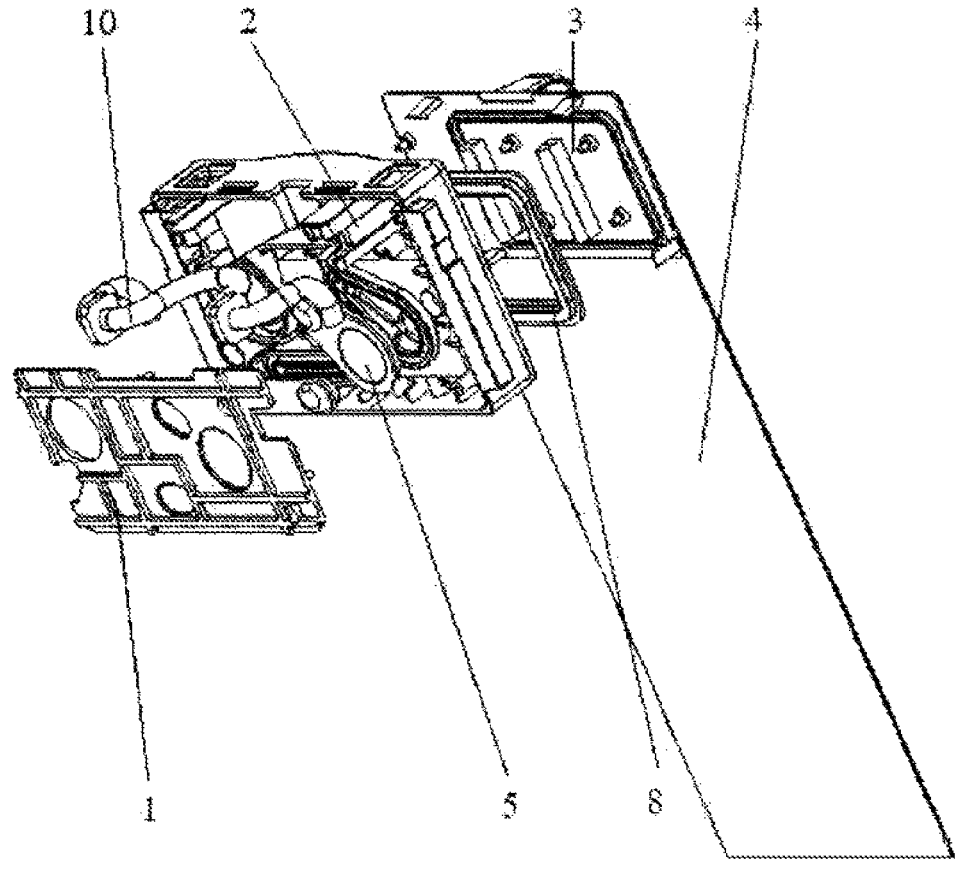
FIG. 1 is an exploded view according to an embodiment of the present invention.
Figure 2:
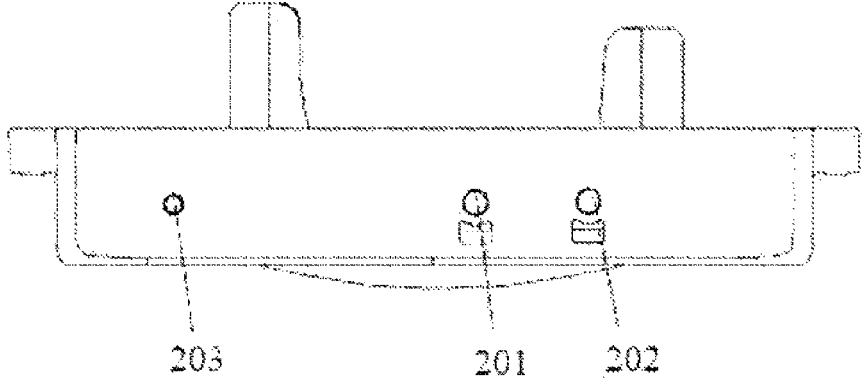
FIG. 2 is a side view according to an embodiment of the present invention.

The present invention is described in following details with the reference to specific implementations shown in the accompanying drawings. However, these implementations are not limited to the present invention, and changes in structure, method, or function that are made by persons with ordinary skills in the art based on these implementations all fall within the protection scope of the present invention.

In the description of the solutions, it should be noted that, terms "center", "up", "down", "left", "right", "front", "rear", "vertical", "horizontal", "inner", "outside", and other orientations or positional relationships are based on the orientations or positional relationship shown in the accompanying drawings, and are only for convenience of description and for simplifying description, rather than being intended to indicate or imply that a device or an element referred to must have a particular orientation or be constructed and operate in a particular orientation. Therefore, these should not be construed as limitation to the present invention. In addition, terms "first", "second", and "third" are merely used for description, and cannot be understood as indicating or implying the relative importance. Moreover, in the description of the solutions, taking an operator as reference, a direction close to the operator is a proximal end, and a direction away from the operator is a distal end.

As shown in FIG. 1 to FIG. 9, the present invention discloses a fluid collection box for phacoemulsification surgery, including a case composed of a front plate 1, a body 2, and a rear plate 3. The case communicates with a waste liquid bag 4. The body 2 has a perfusion passage and a suction passage that are disposed independently. The perfusion passage is a sealed circulation cavity 100 defined by a cover 5 and the body 2. The circulation cavity 100 communicates with a first connection port 201 and a second connection port 202 on the body 2 for perfusion. There is a gap between the cover 5 and the body 2. Connection and disconnection of the perfusion passage is controlled by pressing the cover 5. The suction passage is a pipeline that communicates a third connection port 203 with the waste liquid bag 4, and performs perfusion by a peristaltic pump. The suction passage further communicates with a negative pressure regulating loop, to regulate pressure within the suction passage. The perfusion passage and the suction passage are independently disposed, so that the two do not interfere with each other. In this way, when surges occur, the intraocular fluid is sucked by using the suction passage to regulate intraocular pressure. Meanwhile, it is ensured that pressure within the perfusion passage is stable, thereby reducing changes of the intraocular pressure, and improving safety during use.

Figure 3:
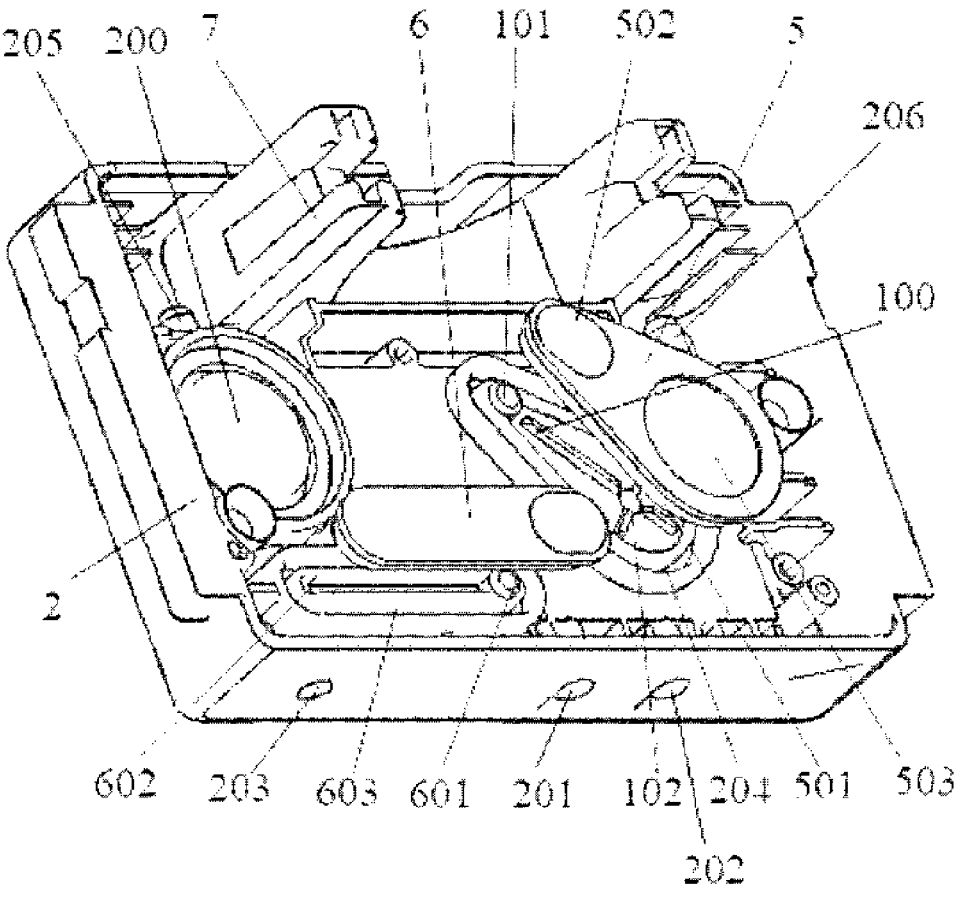
FIG. 3 is a schematic diagram of a partial structure of a body according to the present invention.
Figure 4:
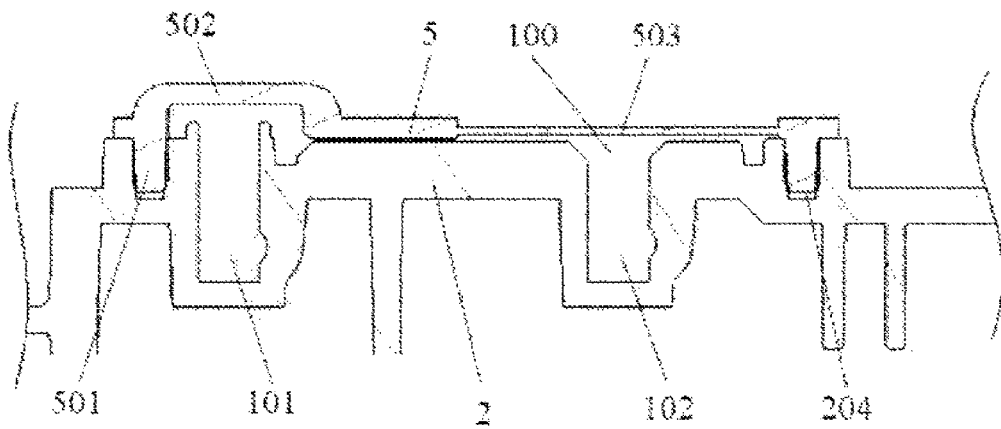
FIG. 4 is a sectional view of a perfusion passage according to the present invention.

Specifically, as shown in FIG. 3 and FIG. 4, a back surface of the cover 5 is provided with a protruding rib 501 extending downward along an edge thereof. The body 2 is provided with a recess 204 matching the protruding rib 501. The protruding rib 501 is in an interference fit with the recess 204 and there is a gap therebetween. A cavity wall of the circulation cavity 100 is defined by the back surface of the cover 5 and a surface of the body 2. A perfusion outlet 101 and a perfusion inlet 102 of the circulation cavity 100 are both located on the body 2. The perfusion outlet 101 communicates with the first connection port 201. The perfusion inlet 102 communicates with the second connection port 202. During perfusion, a perfusion fluid sequentially enters the perfusion inlet 102 from the second connection port 202, flows into the circulation cavity 100, and then flows out of the first connection port 201 through the perfusion outlet 101.

Further, the cover 5 has an outer convex portion 502 and an elastic portion 503. The outer convex portion 502 is opposite to the perfusion outlet 101. The elastic portion 503 is opposite to the perfusion inlet 102. In a first state, there is a gap between the outer convex portion 502 and the perfusion outlet 101, to maintain liquid flow within the circulation cavity 100. In a second state, the outer convex portion 502 is pressed to be closely attached to the perfusion outlet 101, to block the liquid flow within the circulation cavity 100. A linear motion component, such as a solenoid valve, can be disposed outside the outer convex portion 502 for pressing. Structurally, the outer convex portion 502 is disposed opposite to the perfusion outlet 101. Therefore, positioning can be performed quickly when press is required to block the perfusion fluid; on the other hand, the gap between the outer convex portion 502 and the perfusion outlet 101 is increased, which ensures that the perfusion passage has sufficient capacity.

The elastic portion 503 is preferably made of a soft sealing material, such as silica gel or rubber. The elastic portion 503 is a thin film with a thickness between 0.2 mm and 0.6 mm, and can deform during perfusion. The elastic portion 503 is provided with a sensor (not shown in the figures) to detect perfusion pressure within the circulation cavity 100 through the generated deformation. Moreover, the height and the water volume of a matching infusion bottle (not shown in the figures) are determined based on the perfusion pressure. It is an existing technology for the sensor to obtain a pressure value by measuring degree of deformation, which is not the focus of the present invention, and details are not described herein. Elasticity of the elastic portion 503 can also alleviate impact generated when the perfusion fluid enters.

Figure 5:
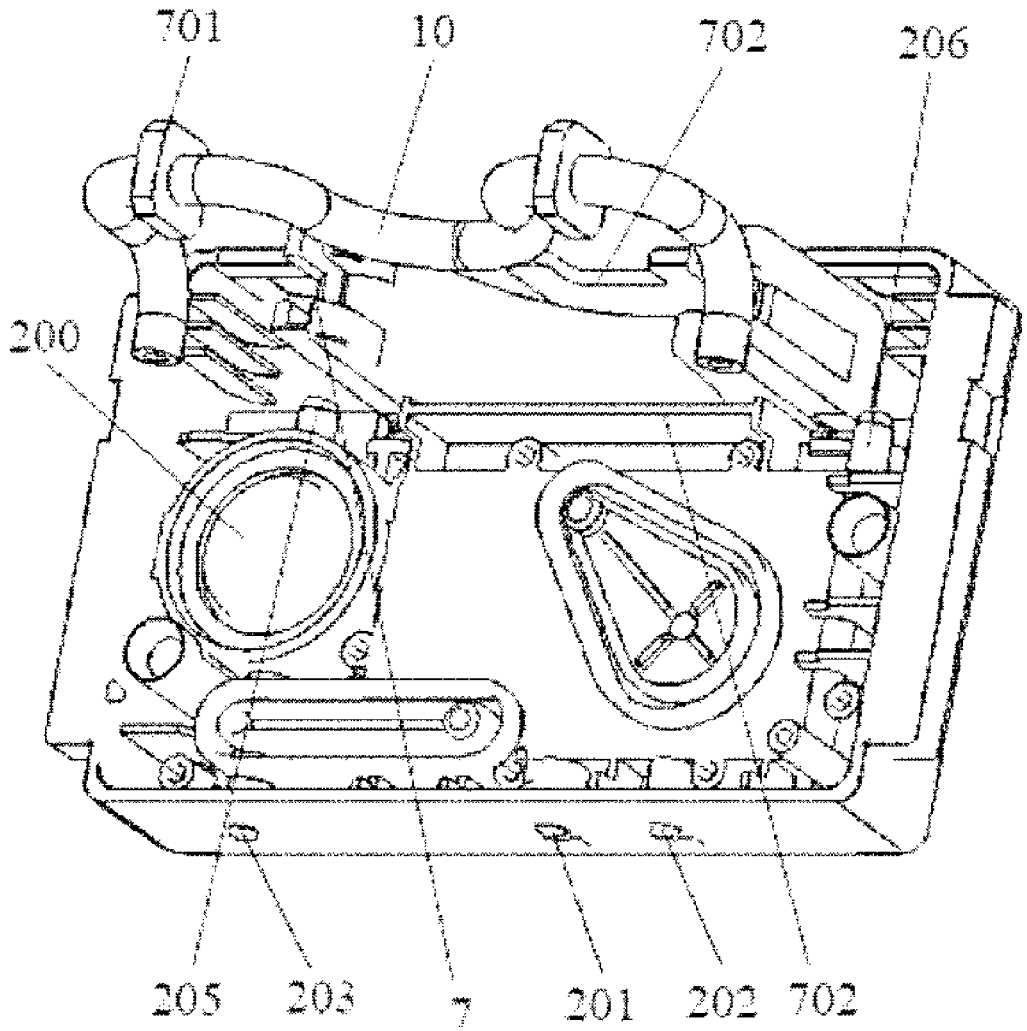
FIG. 5 is a partial schematic diagram according to an embodiment of the present invention.

As shown in FIG. 3 and FIG. 5, the suction passage includes a first communication port 205 and a second communication port 206 on the body 2. The third connection port 203 communicates with the first communication port 205. The waste liquid bag 4 communicates with the second communication port 206. A pump line 10 of the peristaltic pump is communicated between the first communication port 205 and the second communication port 206. The pump line 10 is disposed on a limiting mechanism on the body 2. The limiting mechanism includes a limiting groove 7 fixedly disposed on the body 2 and two fixed blocks 701 clamped at the two ends of the limiting groove 7. Both fixed blocks 701 are firmly connected to the pump line 10. Baffle plates 702 are disposed on the two sides of an extension direction of the pump line 10. Such structure can effectively avoid axial movement and twisting of the pump line 10 during operation, which ensures the stability of the pump line 10.

Figure 6:
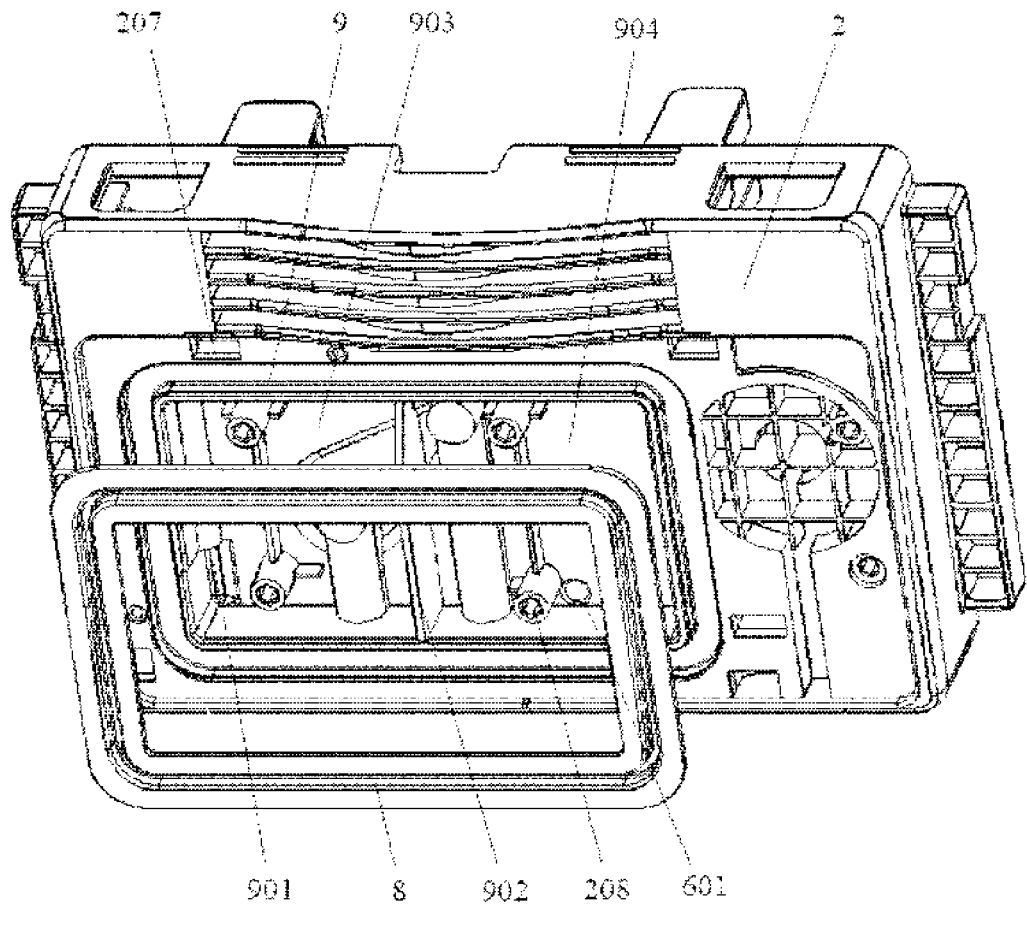
FIG. 6 is a partial schematic diagram according to an embodiment of the present invention.

Further, as shown in FIG. 6, the suction passage includes an accommodation cavity 9 disposed on a back surface of the body 2. The accommodation cavity 9 is a sealed chamber composed of the body 2, the rear plate 3, and a sealing ring 8. In other feasible embodiments, a surface of the rear plate 3 can further be provided with a rear cover matching the sealing ring 8 to further ensure seal ability of the sealed chamber 9.

A liquid inlet 901 of the accommodation cavity 9 communicates with the second communication port 206. The accommodation cavity 9 communicates with the waste liquid bag 4 through communicating members. Specifically, a separator 902 is vertically disposed in the accommodation cavity 9, and divides the accommodation cavity 9 into a first chamber 903 and a second chamber 904. The liquid inlet 901 communicates with the first chamber 903. The top portion of the separator 902 has a notch 9021. The liquid in the first chamber 903 enters the second chamber 904 through the notch 9021. The disposing of the notch 9021 requires the liquid in the first chamber 903 to reach a certain height to flow into the second chamber 904. This structural setting enables the separator 902 to filter out impurities with larger volume in the first chamber 903, thereby preventing the impurities from flowing into the negative pressure regulating loop. Therefore, the goal to prevent large-particle impurities from entering the suction passage through the reflux inlet 601 can be reached. Occurrence of blockage in the suction passage can be reduced. In this preferred embodiment, the separator 902 performs filtering by the notch 9021. In other feasible embodiments, the separator 902 can also be provided with some filtering holes at a top portion thereof for filtering. In the embodiment illustrated in the figure, the notch 9021 is a linear notch. In other feasible embodiments, the notch 9021 can have any suitable shape.

Figure 7:
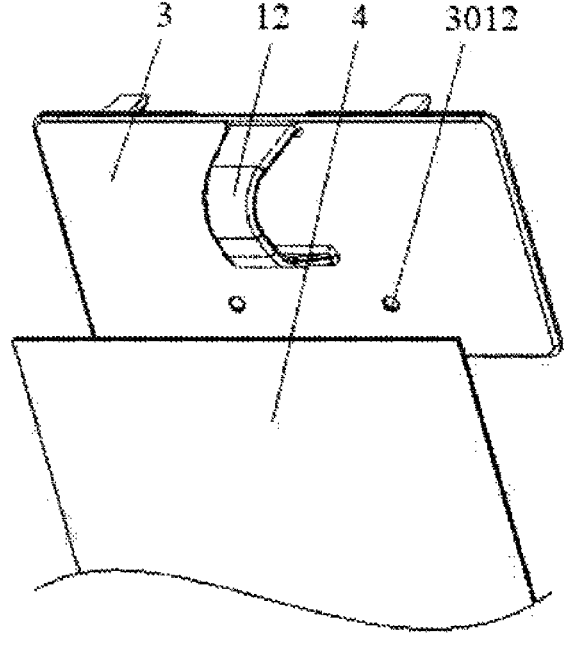
FIG. 7 is a partial schematic diagram of a back surface of a rear plate and a waste liquid bag according to the present invention.
Figure 8:
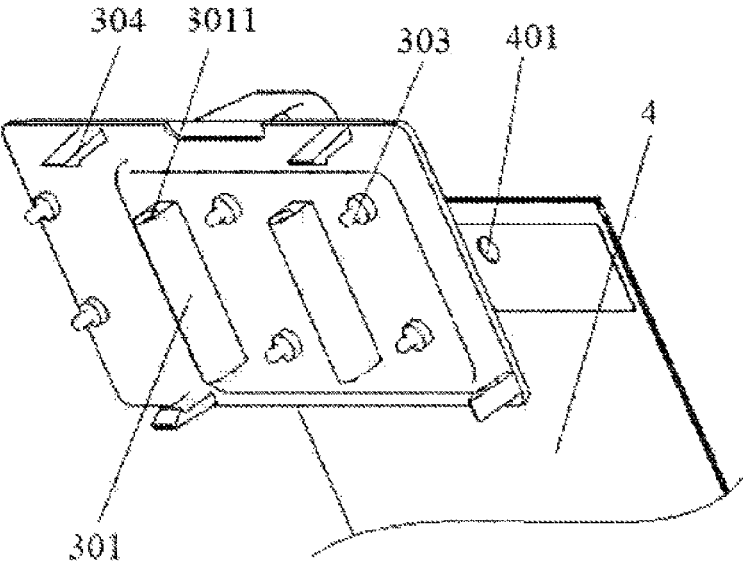
FIG. 8 is a partial schematic diagram of a surface of a rear plate and a waste liquid bag according to the present invention.

As shown in FIG. 7 and FIG. 8, the communicating members are two identical connecting pipes 301 that are vertically disposed on the inner side surface of the rear plate 3. The two connecting pipes 301 are respectively disposed in the first chamber 903 and the second chamber 904. An input port 3011 of the connecting pipe 301 is located at a top portion thereof, and an output port 3012 is located at a bottom portion of a side surface thereof, which is connected to the rear plate 3. The output port 3012 is disposed opposite to and communicates with a through hole 401 on the waste liquid bag 4. The structure of the connecting pipe 301 enables a liquid in the first chamber 903 and the second chamber 904 to be transmitted into the connecting pipe 301 only when a height of the liquid in the first chamber 903 and the second chamber 904 exceeds the input port 3011. Such liquid is transmitted into the waste liquid bag 4 through the output port 3012.

As shown in FIG. 7 and FIG. 8, to ensure a tight connection between the rear plate 3 and the body 2, an inner side surface of the rear plate 3 has a set of clips 302. The body 2 has clamping holes 207 matching the clips 302. The clip 302 can be clamped in the clamping hole 2017, so that the rear plate 3 is clamped with the host 2. Further, an edge of the rear plate 3 is provided with a set of clamping jaws 304 to be clamped with the body 2. The body 2 and the rear plate 3 are also provided with matching positioning holes 208 and positioning pins 303 that are clamped with each other to further strengthen connection stability therebetween.

As shown in FIG. 7, for the ease of fetching, the back surface of the rear plate 3 is provided with a handheld annular component 12. In other feasible embodiments, the component 12 may not be annular, but in any suitable shape, such as circular, square, or elliptical shape.

As shown in FIG. 1, FIG. 3, and FIG. 5, the negative pressure regulating loop is disposed on the surface of the body 2, and is composed of a reflux inlet 601, a reflux outlet 602, and a sealed passage 603. The reflux inlet 601 communicates with the second chamber 904. The reflux outlet 602 communicates with the third connection port 203. The cavity wall of the sealed passage 603 is defined by a sealing cover 6 and the surface of the body 2. When negative pressure in the suction passage reaches a set value, it indicates that the suction passage is blocked at the moment. In this case, the reflux inlet 601 is opened. When the negative pressure in the suction passage is less than the set value, that is, the suction passage is not blocked at the moment, and the reflux inlet 601 is closed. When excessive negative pressure is caused in the suction passage because of a blockage or any other occurring emergency in the suction passage, the disposure of the negative pressure regulating loop can quickly open the reflux inlet 601 to suck the liquid in the second chamber 904 into the suction passage. Such disposure can quickly regulate the negative pressure in the suction passage, thereby avoiding rapid changes of the intraocular pressure, and avoiding occurrence of collapse or significant tissue damages in an eye.

Figure 9:
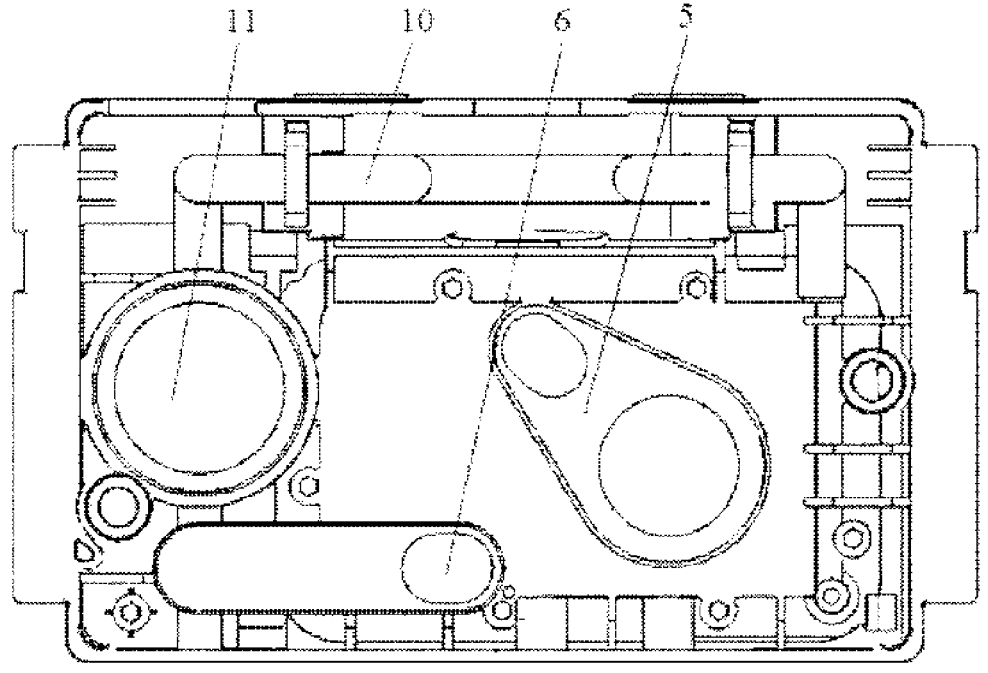
FIG. 9 is a partial schematic diagram according to an embodiment of the present invention.

The negative pressure regulating loop is normally closed, and is opened only when the negative pressure in the suction passage reaches a set value. To control the opening or the closing of the negative pressure regulating loop, a negative-pressure sensor is disposed on the suction message to monitor the negative pressure value within in real-time. As shown in FIG. 9, the negative-pressure sensor is a sealed cavity 200 composed of a deformable thin metal sheet 11 and the surface of the body 2. The sealed cavity 200 respectively communicates with the third connection port 203 and the first communication port 205. The thin metal sheet 11 is preferably made of stainless steel, and therefore has good flexibility. Moreover, the metal sheet 11 can be fixed with the body 2 through injection molding, bonding, and other processes, to ensure sealing of the sealed cavity 200. The sealed cavity 200 is disposed between the third connection port 203 and the first communication port 205 so that the sealed cavity 200 can reflect a value of the negative pressure in the suction passage in real-time through deformation thereof. The sealed cavity 200 also detects the negative pressure value in the suction passage in cooperate with other detection mechanisms (not shown in the figures) provided on the body 2. In this way, the opening or the closing of the negative pressure regulating loop can be controlled based on the measured negative pressure value. Therefore, the precision of pressure control within the suction passage is improved. The detection mechanism can be a pressure sensor, a laser detector, or the like. Obtaining a pressure value by measuring degree of deformation is an existing technology, which is not the focus of the present invention, and details are not described herein.

It should be understood that although this specification is described in accordance with the implementations, not every implementation includes only one independent technical solution. The narrative mode in the description is merely for clarity. A person skilled in the art should take the specifications as a whole, and the technical solutions in all implementations can also be appropriately combined to form other implementations that can be understood by a person skilled in the art.

A series of detailed descriptions listed above are specific descriptions for the feasible implementations of the present invention, and are not intended to limit the protection scope of the present invention. Any equivalent implementation or modification made without departing from the technical spirit of the present invention shall fall within the protection scope of the present invention.

What is claimed is:

1. A fluid collection box for phacoemulsification surgery, comprising a case composed of a front plate, a body, and a rear plate, wherein the case communicates with a waste liquid bag; the body has a perfusion passage and a suction passage that are disposed independently; the perfusion passage is a sealed circulation cavity defined by a cover and the body; the circulation cavity communicates with a first connection port and a second connection port on the body for perfusion; there is a gap between the cover and the body, and connection and disconnection of the perfusion passage is controlled by pressing the cover; the suction passage is a pipeline that communicates a third connection port with the waste liquid bag, and performs perfusion by a peristaltic pump; and the suction passage further communicates with a negative pressure regulating loop, to regulate pressure within the suction passage.

2. The fluid collection box for phacoemulsification surgery according to claim 1, wherein a back surface of the cover is provided with a protruding rib extending downward along an edge thereof; the body is provided with a recess matching the protruding rib; the protruding rib is in an interference fit with the recess and there is a gap therebetween; a cavity wall of the circulation cavity is defined by the back surface of the cover and a surface of the body; a perfusion outlet and a perfusion inlet of the circulation cavity are both located on the body; the perfusion outlet communicates with the first connection port; and the perfusion inlet communicates with the second connection port.

3. The fluid collection box for phacoemulsification surgery according to claim 2, wherein the cover has an outer convex portion and an elastic portion; the outer convex portion is opposite to the perfusion outlet; the elastic portion is opposite to the perfusion inlet; in a first state, there is a gap between the outer convex portion and the perfusion outlet, to maintain liquid flow within the circulation cavity; in a second state, the outer convex portion is pressed to be closely attached to the perfusion outlet, to block the liquid flow within the circulation cavity; the elastic portion can deform during perfusion; and the elastic portion is provided with a sensor to detect perfusion pressure within the circulation cavity through the generated deformation.

4. The fluid collection box for phacoemulsification surgery according to claim 1, wherein the suction passage comprises a first communication port and a second communication port both on the body; the third connection port communicates with the first communication port; the waste liquid bag communicates with the second communication port; a pump line of the peristaltic pump is connected between the first communication port and the second communication port; the pump line is disposed on a limiting mechanism on the body; the limiting mechanism comprises a limiting groove fixedly disposed on the body and two fixed blocks clamped at the two ends of the limiting groove; each of the fixed blocks is fixedly connected to the pump line; and baffle plates are disposed on the two sides of an extension direction of the pump line.

5. The fluid collection box for phacoemulsification surgery according to claim 4, wherein the suction passage comprises an accommodation cavity disposed on a back surface of the body; the accommodation cavity is a sealed chamber composed of the body, the rear plate, and a sealing ring; a liquid inlet of the accommodation cavity communicates with the second communication port; and the accommodation cavity communicates with the waste liquid bag by communicating members.

6. The fluid collection box for phacoemulsification surgery according to claim 5, wherein a separator is vertically disposed in the accommodation cavity, and the accommodation cavity is divided into a first chamber and a second chamber by the separator; the liquid inlet communicates with the first chamber; a top portion of the separator has a notch; and liquid in the first chamber enters the second chamber through the notch.

7. The fluid collection box for phacoemulsification surgery according to claim 6, wherein the communicating members are two identical connecting pipes that are vertically disposed on an inner side surface of the rear plate; the two connecting pipes are respectively disposed in the first chamber and the second chamber; an input port of each of the two connecting pipes is located at a top portion thereof, and an output port of each of the two connecting pipes thereof is located at a bottom portion of a side surface, where each of the two connecting pipes and the rear plate connect; and each of the output ports of the two connecting pipes is disposed opposite to and communicates with a through hole on the waste liquid bag.

8. The fluid collection box for phacoemulsification surgery according to claim 7, wherein the negative pressure regulating loop is disposed on the surface of the body, and is composed of a reflux inlet, a reflux outlet, and a sealed passage; the reflux inlet communicates with the second chamber; the reflux outlet communicates with the third connection port; a cavity wall of the sealed passage is defined by a sealing cover and the surface of the body; when the suction passage is detected blocked, the reflux inlet will be opened; and the reflux inlet will be closed when the suction passage is not blocked.

9. The fluid collection box for phacoemulsification surgery according to claim 8, wherein a negative pressure value in the suction passage is measured by a negative-pressure sensor disposed on the surface of the body; the negative-pressure sensor is a sealed cavity composed of a deformable thin metal sheet and the surface of the body; and the sealed cavity respectively communicates with the third connection port and the first communication port.

10. The fluid collection box for phacoemulsification surgery according to claim 9, wherein a back surface of the rear plate is provided with a handheld annular component.

11. The fluid collection box for phacoemulsification surgery according to claim 2, wherein the suction passage comprises a first communication port and a second communication port both on the body; the third connection port communicates with the first communication port; the waste liquid bag communicates with the second communication port; a pump line of the peristaltic pump is connected between the first communication port and the second communication port; the pump line is disposed on a limiting mechanism on the body; the limiting mechanism comprises a limiting groove fixedly disposed on the body and two fixed blocks clamped at the two ends of the limiting groove; each of the fixed blocks is fixedly connected to the pump line; and baffle plates are disposed on the two sides of an extension direction of the pump line.

12. The fluid collection box for phacoemulsification surgery according to claim 3, wherein the suction passage comprises a first communication port and a second communication port both on the body; the third connection port communicates with the first communication port; the waste liquid bag communicates with the second communication port; a pump line of the peristaltic pump is connected between the first communication port and the second communication port; the pump line is disposed on a limiting mechanism on the body; the limiting mechanism comprises a limiting groove fixedly disposed on the body and two fixed blocks clamped at the two ends of the limiting groove; each of the fixed blocks is fixedly connected to the pump line; and baffle plates are disposed on the two sides of an extension direction of the pump line.

* * * * *